(12) United States Patent
Van Krieken et al.

(10) Patent No.: US 10,577,339 B2
(45) Date of Patent: Mar. 3, 2020

(54) METHOD FOR MANUFACTURING FURAN-2,5-DICARBOXYLIC ACID (FDCA) FROM A SALT SOLUTION

(71) Applicant: PURAC BIOCHEM BV, Gorinchem (NL)

(72) Inventors: Jan Van Krieken, Gorinchem (NL); Andre Banier De Haan, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 15/558,244

(22) PCT Filed: Mar. 17, 2016

(86) PCT No.: PCT/EP2016/055820
§ 371 (c)(1),
(2) Date: Sep. 14, 2017

(87) PCT Pub. No.: WO2016/146753
PCT Pub. Date: Sep. 22, 2016

(65) Prior Publication Data
US 2018/0044312 A1    Feb. 15, 2018

(30) Foreign Application Priority Data
Mar. 17, 2015 (EP) .................................. 15159401

(51) Int. Cl.
*C07D 307/68* (2006.01)
(52) U.S. Cl.
CPC ................................ *C07D 307/68* (2013.01)
(58) Field of Classification Search
CPC .................................................... C07D 307/68
See application file for complete search history.

(56) References Cited

U.S. PATENT DOCUMENTS 9,061,986 B2 * 6/2015 De Haan ................ C01B 7/035

FOREIGN PATENT DOCUMENTS

| KR | 2014-0057607 A | 5/2014 |
|---|---|---|
| WO | 2011/026913 A1 | 3/2011 |
| WO | 2013/025106 A1 | 2/2013 |
| WO | 2013025106 * | 2/2013 |
| WO | 2013/093043 A1 | 6/2013 |

OTHER PUBLICATIONS

Jun. 22, 2016 International Search Report issued in International Patent Application No. PCT/EP2016/055820.
Jun. 22, 2016 Written Opinion issued in International Patent Application No. PCT/EP2016/055820.
Apr. 15, 2018 Office Action issued in Korean Patent Application No. 10-2017-7029395.
Apr. 15, 2018 Office Action issued in Korean Patent Application No. 10-2017-7029396.
Aug. 30, 2019 Office Action issued in Indian Patent Application No. 201747031919.

* cited by examiner

*Primary Examiner* — D Margaret M Seaman
(74) *Attorney, Agent, or Firm* — Oliff PLC

(57) ABSTRACT

A method for manufacturing furan-2,5-dicarboxylic acid (FDCA) by converting a furan-2,5-dicarboxylate salt (MFDC) into FDCA, including the steps of combining an aqueous solution of MFDC with a concentration of at least 5 wt. % with an inorganic acid (HY), to form a reaction mixture including solid FDCA in a concentration of 1-15 wt. % in a salt solution resulting from the cation of furan-2,5-dicarboxylate salt and the anion of the inorganic acid (MY solution), removing solid FDCA from the reaction mixture in a solid/liquid separation step, and providing part of the MY solution resulting from the solid/liquid separation step to the step of combining MFDC with HY. The step of providing part of MY salt solution resulting from the solid/liquid separation step to the step of combining MFDC with HY makes it possible to obtain a stable and economic process which results in an FDCA product with good quality and high yield.

10 Claims, 1 Drawing Sheet

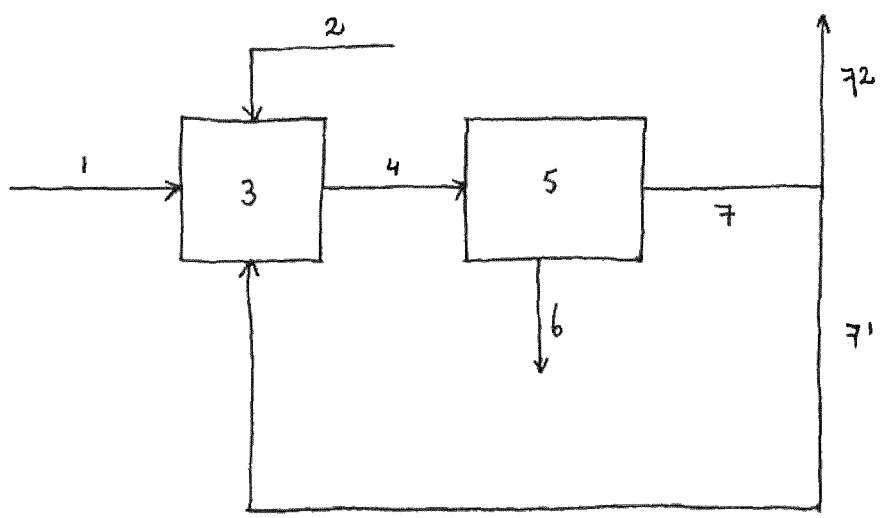

METHOD FOR MANUFACTURING FURAN-2,5-DICARBOXYLIC ACID (FDCA) FROM A SALT SOLUTION

The present invention pertains to a method for manufacturing furan-2,5-dicarboxylic acid (FDCA) from a salt solution.

FDCA is an attractive material for numerous applications, among others as starting material for polymer production, where FDCA-based copolymers are an alternative to, among others, polyethylene terephthalic acid polymers (PET). FDCA esters may also find use as plasticizers or crosslinkers. The dimethylester of FDCA may be of particular interest for polymerisation. Esters of higher alcohols, e.g., dibutyl FDCA, diethylhexyl FDCA, and dioctyl FDCA may be of particular interest for use as plasticizers and in polymers and coatings.

FDCA can be manufactured through various methods. One method, which is particularly attractive is a fermentation-based process starting from renewable resources. In this manner, FDCA can be obtained in an environmentally friendly manner.

As is known in the art, the manufacture of FDCA through fermentation generally takes the form of a fermentative biooxidation of 5-(hydroxymethyl) furfural (HMF). This is, e.g., described in WO2011/026913. The liquid wherein the process is carried out is called the fermentation broth or the fermentation medium. The formation of FDCA in the process will result in a decrease of the pH of the fermentation broth. Since such a decrease in pH can damage the micro-organism's metabolic process, a neutralizing agent, i.e. a base, is often added to the fermentation medium in order to neutralize the pH or to maintain an optimum pH value for the micro-organisms.

In consequence, the FDCA produced in the fermentation medium is typically present in the form of a salt, which may be dissolved in the fermentation medium, present in the form of a solid salt, or both dissolved in the fermentation medium and present in the form of a solid salt.

To convert the salt of FDCA to the acid, it has been envisaged to react the salt of FDCA with an inorganic acid, to yield FDCA and a salt built up from the cation of the salt of FDCA and the anion of the inorganic acid. However, while this reaction is simple and elegant in theory, it has been found that when carrying it out in practice, various operational problems occur, which make it difficult to operate the reaction in a stable an economically attractive manner, while obtaining FDCA with high product quality.

A particular issue resides in the solubility of the various components and the properties of the product formed. FDCA has a low solubility in water. In theory, this would be expected to make it easy to separate the FDCA from an aqueous mixture containing the other reactant components. However, due to the specific shape of the FDCA crystals, it has been found that concentrated suspensions of FDCA are difficult to process. On the other hand, dilution of the FDCA suspension leads to a loss in yield because more FDCA will dissolve. A problem which occurs in particular in the processing of solutions of soluble FDCA salts in combination with acid solutions is that the large amount of water in the system results in the loss of FDCA to the product streams. There is therefore need in the art for a process which allows manufacture of FDCA from solutions of soluble FDCA salts which method generates a high product yield in combination with good processing properties.

The present invention provides a method for manufacturing furan-2,5-dicarboxylate (FDCA) by converting a salt of furan-2,5-dicarboxylate (MFDC) into furan-2,5-dicarboxylate (FDCA), which allows stable operation in an economically attractive manner, while obtaining FDCA with high product quality and high yield.

The present invention pertains to a method for manufacturing furan-2,5-dicarboxylic acid (FDCA) by converting a furan-2,5-dicarboxylate salt (MFDC) into furan-2,5-dicarboxylic acid (FDCA), comprising the steps of
  combining an aqueous solution of MFDC with a concentration of at least 5 wt. % with an inorganic acid (HY), to form a reaction mixture comprising solid FDCA in a concentration of 1-15 wt. % in a solution of a salt resulting from the cation of the furan-2,5-dicarboxylate salt and the anion of the inorganic acid (MY solution),
  removing solid FDCA from the reaction mixture in a solid/liquid separation step, and
  providing part of the MY solution resulting from the solid/liquid separation step to the step of combining MFDC with HY.

Not wishing to be bound by theory, it is believed that the step of providing part of the MY salt solution resulting from the solid/liquid separation step to the step of combining MFDC with HY makes it possible to obtain a stable and economic process which results in an FDCA product with good quality, and obtained in high yield. Various further advantages of the present invention and its specific embodiments will be discussed in more detail below.

The present invention will be elucidated with reference to the following FIGURE, without being limited thereto or thereby.

FIG. 1 illustrates a first embodiment of the present invention.

In FIG. 1, a solution of furan-2,5-dicarboxylate salt (MFDC) is provided through line (1) to a reaction vessel (3). Inorganic acid (HY) is provided to reaction vessel (3) through line (2). The reaction vessel is also provided with a salt solution (MY solution) through line (71). In the reaction vessel, MFDC reacts with HY to form FDCA and MY, and the reaction mixture comprising FDCA and HY is transferred through line (4) to a solid/liquid separation step (5). Although not depicted in FIG. 1, it is of course also possible to carry out the solid liquid separation step in the reaction vessel. In solid liquid separation step (5), the solid FDCA is separated from the MY salt solution, and withdrawn through line (6). The salt solution is withdrawn through line (7). Part of the salt solution is provided to reaction vessel (3) through line (71). Another part of the salt solution is withdrawn through line (72).

The method according to the invention starts out from an aqueous solution of a salt of furan-2,5-dicarboxylic acid (MFDC). The solution has an MFDC concentration of at least 5 wt. %, in particular at least 10 wt. %. The maximum is determined by the solubility of the MFDC. As a general maximum, a value of 30 wt. % may be mentioned.

The furan-2,5-dicarboxylate salt is preferably selected from sodium furan-2,5-dicarboxylate (NaFDC), potassium furan-2,5-dicarboxylate (KFDC), and ammonium furan-2,5-dicarboxylate (NH4FDC). These salts have been found to be attractive as starting materials because they can be obtained relatively easy, e.g., from fermentation processes. On the other hand, it has been found that when they are used in the process according to the invention, FDCA is obtained in high yield and with high product quality and process efficiency.

Due to their high solubility in water NaFDC, KFDC, and NH4FDC, can be provided in the form of concentrated solutions. In one embodiment, the MFDC, preferably selected from NaFDC, KFDC, and NH4FDC, is thus applied in the form of a solution, with a concentration of at least 10 wt. %. The maximum concentration of a solution is determined by the solubility of the salt in water and can be determined by the skilled person on a case by case basis.

The MFDC is combined with an inorganic acid (HY), to form a reaction mixture comprising solid FDCA in a solution of a salt resulting from the cation of the MFDC and the anion of the inorganic acid (MY solution).

In the process according to the invention, the combination of acid and salt has to be selected in such a manner that the cation M of the MFDC and the anion Y of the inorganic acid HY results in the formation of a salt with a solubility in water which is so high that no salt precipitates under process conditions.

The inorganic acid added in the process according to the invention serves to convert the FDCA salt to the acid. Depending on the nature of the inorganic acid and on the other components present in the system, the inorganic acid can be provided in the form of an aqueous solution, or, e.g., in the case of hydrochloric acid, in gaseous form. The inorganic acid is generally a strong inorganic acid, i.e., an acid with pKa of below zero. Examples of suitable acids are sulphuric acid, hydrochloric acid, nitric acid, phosphoric acid, hydrobromic acid, and derivatives thereof such as $NH_4HSO_4$. The use of sulphuric acid, hydrochloric acid, and nitric acid, may be preferred, with the use of hydrochloric acid being particularly preferred.

The acid concentration of an aqueous solution is generally not critical to the present invention. Concentrated solutions, e.g., with an acid concentration of at least 5%, in particular at least 10%, more in particular at least 15 wt. %, are generally preferred for reasons of process economy. The maximum concentration will be determined to the solubility or miscibility of the acid in question. A general value of at most 35 wt. % may be mentioned. The use of concentrated HY solutions is preferred because it limits the amount of water in the system.

The amount of acid to be added will generally be at least sufficient to neutralise the FDCA salt. This can easily be calculated from the amount of FDCA salt present, and be determined by monitoring the pH of the reaction medium. It is preferred for the pH of the reaction medium to be at most 2. It may be preferred for the pH of the reaction medium to be in the range of 1 to 2, to combine a high FDCA yield with the avoidance of a high excess of acid, as this may be detrimental to processing apparatus, or may result in unnecessary recycle of materials.

In the method according to the invention, the amount of MFDC and its water content, the amount of acid and its concentration, and the amount of MY solution which are combined will be selected in such a manner that the FDCA concentration in the reaction mixture is within the range of 1-15 wt. %, in particular 1-10 wt. %. If the amount of FDCA in the reaction mixture is below 1 wt. %, the volume stream to be processed is unnecessarily large. On the other hand, if the amount of FDCA formed is above 15 wt. % it has been found that the processability of the reaction mixture and the subsequent solid liquid separation are detrimentally affected. In some cases it may be preferred for the amount and concentration of the various components to be selected such that the amount of FDCA formed is within the range of 2 to 8 wt. %, in particular 3-7 wt. %, calculated on the total weight of the reaction mixture. The amount of FDCA here is the amount of solid FDCA. As FDCA has a low solubility in this system, the total amount of FDCA and the amount of solid FDCA are about equal.

The solid FDCA is removed from the reaction mixture in a solid/liquid separation step. The solid/liquid separation step can be carried out by methods known in the art, e.g., methods encompassing one or more of filtration, centrifugation, sedimentation, or using hydrocyclones. The use of filtration is often preferred.

The FDCA separated in the solid liquid separation step can be processed as desired. If so desired it can be subjected to a washing step.

After removal of the solid FDCA, a salt solution remains, of which the cation corresponds with the cation of the original FDCA salt (M), and the anion corresponds to the anion of the inorganic acid (Y). It is a feature of the present invention that of the salt solution remaining after the solid/liquid separation step, a part is recycled to the step of combining the salt of FDCA with the inorganic acid.

The amount of MY solution which is recycled is selected such that the amount of solid FDCA formed is within the ranges stipulated above. The amount of MY solution which is recycled thus also depends on the concentration of the acid provided, and on the form in which the MFDC is provided. It is preferred for a substantial part of the MY solution to be provided to the step of combining the salt of FDCA with the inorganic acid.

It has been found that the presence of a relatively large amount of MY solution in the step of combining MFDC with HY results in a higher FDCA yield. Not wishing to be bound by theory, it is believed that this is caused by the fact that the solubility of FDCA in an MY solution is, at least for some salts, lower that the solubility of FDCA in water. Therewith, the presence of the salt solution is believed to result in increased precipitation of solid FDCA as compared to a system wherein a corresponding amount of water would be present. In one embodiment at least 40 vol. % of the MY solution resulting from the solid/liquid separation step is provided to the step of combining MFDC with HY, in particular at least 50 vol. %, more in particular at least 60 vol. %, in some embodiments at least 70 vol. % and/or at most 95 vol. %.

The concentration of the MY solution withdrawn from the solid liquid separation step may vary within wide ranges. As a minimum, a value of at least 5 wt. % may be mentioned, in particular at least 10 wt. %. The upper limit will be determined by the solubility of the MY salt. As a general maximum, a value of 30 wt. % may be mentioned. A range of 10-20 wt. % may be preferred.

In one embodiment, the present invention pertains to a method for manufacturing furan-2,5-dicarboxylic acid (FDCA) by converting a furan-2,5-dicarboxylate salt selected from NaFDC, KFDC, and NH4FDC into furan-2, 5-dicarboxylic acid (FDCA), comprising the steps of combining an aqueous solution of MFDC with a concentration of 5-30 wt. % with an inorganic acid (HY), to form a reaction mixture comprising solid FDCA in a concentration of 1-15 wt. % in a solution of a salt resulting from the cation of the furan-2,5-dicarboxylate salt and the anion of the inorganic acid (MY solution), removing solid FDCA from the reaction mixture in a solid/liquid separation step, and providing 40-95 wt. % of the MY solution resulting from the solid/liquid separation step to the step of combining MFDC with HY.

The specific preferences described above also apply to this process.

The MFDC can, e.g., be obtained from a fermentation process, wherein an aqueous feed comprising an FDCA salt is formed. Such a step typically comprises the substeps of fermenting a carbon source by means of a micro-organism, and forming a fermentation medium comprising FDCA, and, generally during fermentation (partially) neutralizing the fermentation medium in order to establish a desirable pH by adding a neutralizing agent, i.e. a base. Suitable bases include oxides, hydroxides, and carbonates of sodium, potassium, and ammonium.

As indicated above, the manufacture of FDCA through fermentation generally takes the form of a fermentative biooxidation of 5-(hydroxymethyl) furfural (HMF). These processes are known in the art and it is within the scope of the skilled person to select a fermentation process leading to the formation of FDCA.

The fermentation medium is generally subjected to a biomass removal step. Biomass can, e.g., be removed by (ultra)filtration, centrifugation or decantation of the biomass. Biomass removal has been found to result in an end product with improved properties.

Where the FDCA salt is soluble in water, after biomass removal, a solution comprising dissolved FDCA salt is thus obtained, which can be used as starting material in the process according to the invention, optionally after further purification and/or water removal steps.

Where the fermentation broth comprises FDCA salt in the solid state, the FDCA salt can be separated from the fermentation broth via solid-liquid separation methods such as filtration, or one of the other methods discussed above. The solid FDCA salt thus obtained can be used as starting material in the process according to the invention, optionally after further purification steps.

It will be evident to the skilled person that the various aspects of the present invention which are described above in different paragraphs may be combined.

The invention will be elucidated by the following example, without being limited thereto or thereby.

EXAMPLE 1

Acidulation of 30 wt. % Na2FDC with 100% H2SO4 and Recycle of Motherliquor (Model Example)

The following experimental setup was modelled in a computer using known solubility data of the various compounds. A stirred reactor was charged with 210 g of a 19.9 wt. % sodium sulphate (Na2SO4) solution and controlled at 40° C. Sodium furan-2,5-dicarboxylate tetrahydrate (Na2FDC.4H2O, 20 g, 73 mmol) was dissolved in 30 g of water, simulating a nearly saturated solution. This solution was added to the reactor. Sulphuric acid 96% (7.5 g, 73 mmol) was added to the reactor in order to form FDCA.

The resulting mixture contained 5.3 wt. % of FDCA. The solid FDCA was separated by means of filtration. The clear filtrate contained 19.9 wt. % of Na2SO4, which is below the saturation concentration at 40° C. (32.8%), but above the solubility at room temperature (16.3 wt. %).

The 210 g of a 19.9 wt. % sodium sulphate (Na2SO4) solution corresponds to a recycle of sodium sulphate solution of 83 vol. %.

The invention claimed is:

1. Method for manufacturing furan-2,5-dicarboxylic acid (FDCA) by converting a furan-2,5-dicarboxylate salt (MFDC) into furan-2,5-dicarboxylic acid (FDCA), comprising the steps of
combining an aqueous solution of MFDC with a concentration of at least 5 wt. % with an inorganic acid (HY), to form a reaction mixture comprising solid FDCA in a concentration of 1-15 wt. % in a solution of a salt resulting from the cation of the furan-2,5-dicarboxylate salt and the anion of the inorganic acid (MY solution),
removing solid FDCA from the reaction mixture in a solid/liquid separation step, and
providing part of the MY solution resulting from the solid/liquid separation step to the step of combining MFDC with HY.

2. Method for manufacturing furan-2,5-dicarboxylic acid (FDCA) by converting a furan-2,5-dicarboxylate salt (MFDC) into furan-2,5-dicarboxylic acid (FDCA), comprising the steps of
combining an aqueous solution of MFDC with a concentration of at least 5 wt. % with an inorganic acid (HY), to form a reaction mixture comprising solid FDCA in a concentration of 1-15 wt. % in a solution of a salt resulting from the cation of the furan-2,5-dicarboxylate salt and the anion of the inorganic acid (MY solution),
removing solid FDCA from the reaction mixture in a solid/liquid separation step, and
providing part of the MY solution resulting from the solid/liquid separation step to the step of combining MFDC with HY,
wherein the furan-2,5-dicarboxylate salt is selected from sodium furan-2,5-dicarboxylate (NaFDC), potassium furan-2,5-dicarboxylate (KFDC), and ammonium furan-2,5-dicarboxylate (NH4FDC).

3. Method according to claim 1, wherein the MFDC is provided in the form of an aqueous solution with a concentration of at least 10 wt. %.

4. Method according to claim 1, wherein the inorganic acid (HY) is selected from hydrochloric acid (HCl), nitric acid ($HNO_3$), and sulphuric acid ($H_2SO_4$).

5. Method according to claim 1, wherein the amount of MFDC and its water content, the amount of acid and its concentration, and the amount of MY solution which are combined are selected in such a manner that the FDCA concentration in the reaction mixture is within the range of 1-10 wt. %, calculated on the total weight of the reaction mixture.

6. Method according to claim 1, wherein at least 40 vol. % of the MY solution resulting from the solid/liquid separation step is provided to the step of combining MFDC with HY.

7. Method according to claim 1 wherein the concentration of the MY solution withdrawn from the solid liquid separation step has a concentration of at least 5 wt. %.

8. Method for manufacturing furan-2,5-dicarboxylic acid (FDCA) by converting a furan-2,5-dicarboxylate salt (MFDC) into furan-2,5-dicarboxylic acid (FDCA), comprising the steps of
combining an aqueous solution of MFDC with a concentration of 5-30 wt. % with an inorganic acid (HY), to form a reaction mixture comprising solid FDCA in a concentration of 1-15 wt. % in a solution of a salt resulting from the cation of the furan-2,5-dicarboxylate salt and the anion of the inorganic acid (MY solution),
removing solid FDCA from the reaction mixture in a solid/liquid separation step, and
providing 40-95 wt. % of the MY solution resulting from the solid/liquid separation step to the step of combining MFDC with HY,
wherein the furan-2,5-dicarboxylate salt is selected from NaFDC, KFDC, and NH4FDC.

9. Method according to claim 1 wherein the MFDC results from a fermentation step.

10. Method according to claim 1, wherein of the HY solution resulting from the solid/liquid separation step, a part is recycled to the combination step, and another part is not recycled to the combination step.

\* \* \* \* \*